(12) United States Patent
Sun et al.

(10) Patent No.: US 8,512,700 B2
(45) Date of Patent: Aug. 20, 2013

(54) ANTIBODY PROTECTIVE AGENT AND METHODS OF USING SAME

(75) Inventors: Xiulan Sun, WuXi (CN); Yinzhi Zhang, WuXi (CN); Zaijun Li, WuXi (CN); Jingping Zhang, WuXi (CN); Weimin Niu, WuXi (CN)

(73) Assignees: Jiangnan University, WuXi, JS (CN); Wuxi Center for Disease Control and Prevention, Wuxi, JS (CN)

( * ) Notice: Subject to any disclaimer, the term of this patent is extended or adjusted under 35 U.S.C. 154(b) by 407 days.

(21) Appl. No.: 12/848,138

(22) Filed: Jul. 31, 2010

(65) Prior Publication Data
US 2011/0262626 A1    Oct. 27, 2011

(30) Foreign Application Priority Data
Apr. 22, 2010   (CN) .......................... 2010 1 0152395

(51) Int. Cl.
*A61K 39/395*    (2006.01)
(52) U.S. Cl.
USPC ........................................ 424/130.1; 435/41

(58) Field of Classification Search
CPC ........................................................ C12P 1/00
USPC ................................................................ 435/41
See application file for complete search history.

(56) References Cited

U.S. PATENT DOCUMENTS
2007/0059789 A1*   3/2007   Bornscheuer et al. .......... 435/41

* cited by examiner

*Primary Examiner* — Dah-Wei Yuan
*Assistant Examiner* — Andrew Bowman
(74) *Attorney, Agent, or Firm* — Lili Chen

(57) ABSTRACT

The invention provides an effective and environmentally friendly antibody protective agent and the methods of using it in immunological detection. The antibody protective agent helps antibody to maintain relatively high immunological activity at room temperature. Working electrodes coated with antibodies and the antibody protective agent are installed in immunological detection devices to enhance stability and accuracy of immunological detection. The antibody protective agent is effectively used in the detection of a variety of toxins, for example, aflatoxin, staphylococcal enterotoxin, algae toxin, and vomitoxin.

6 Claims, 4 Drawing Sheets

ANTIBODY PROTECTIVE AGENT AND METHODS OF USING SAME

CROSS-REFERENCE TO RELATED APPLICATIONS

Figure 1:
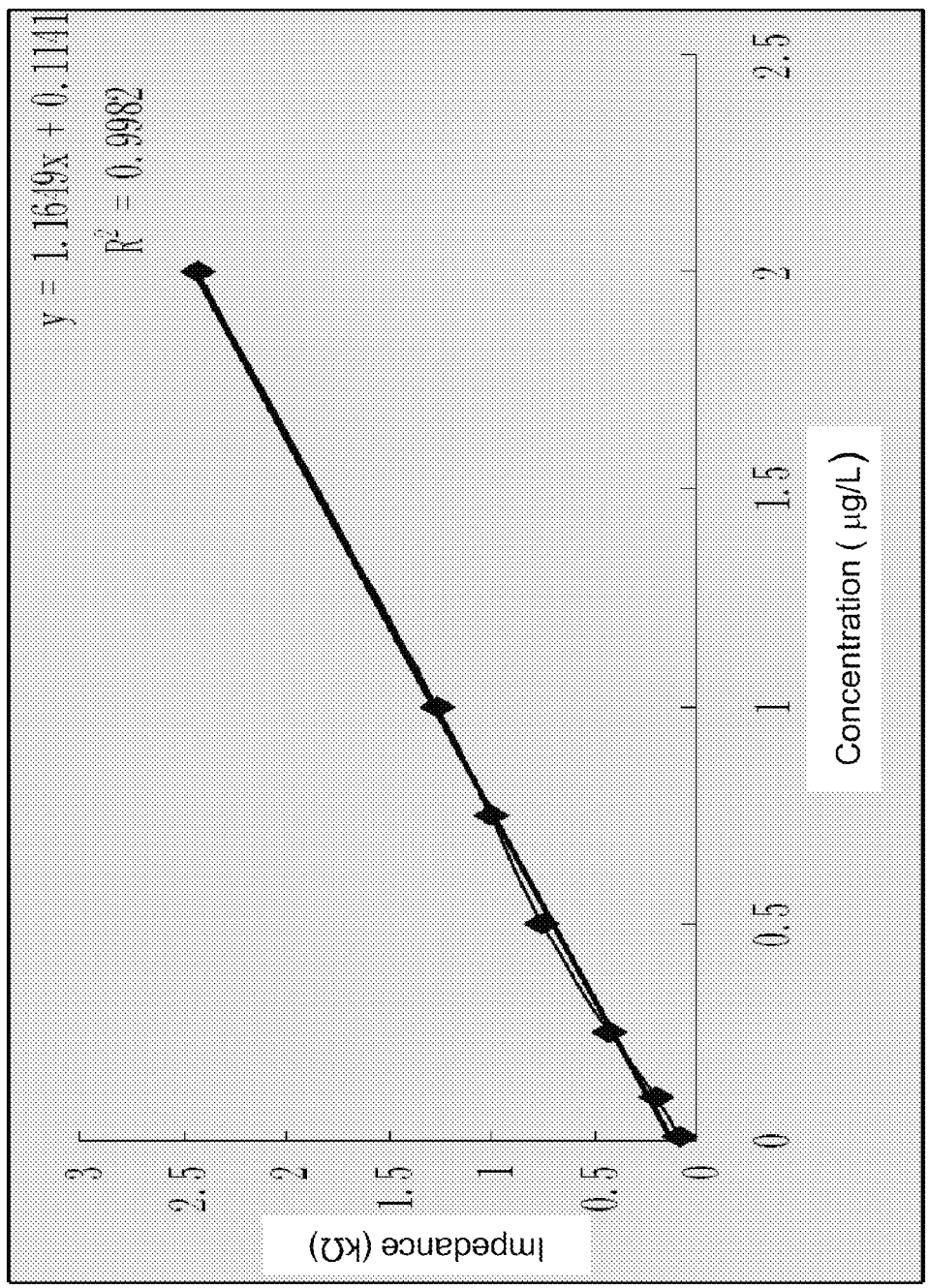

This application claims priority of Chinese Application Serial No. 201010152395.9, entitled "An Antibody Protective Agent and Methods of Using Same", filed Apr. 22, 2010, which is herein incorporated by reference in its entirety.

BACKGROUND OF THE INVENTION

1. Field of the Invention

This invention is in the field of protein protective agents, and in particular relates to an antibody protective agent that can be used in immunological detection.

2. Description of the Related Art

Ionic liquid is a liquid system completely made by ionic substances at room temperature (generally under 100° C.). It is generally composed of organic cations, inorganic anions and organic anions. The composition of these cations and anions jointly determines the characteristics of such ionic liquid.

Ionic liquids have many unique physical and chemical properties. For example, many ionic liquids composed of imidazolium cations decompose at a temperature as high as 400° C.

As ionic liquids generally melt below 100° C., they are in stable liquid state within the temperature range from 300° C. to 400° C., which are distinct from ordinary solvents.

The ionic bond between the ions of ionic liquids is usually stronger than the Van der Waash forces between the molecules of ordinary liquids. For example, the ionic bond is 10 times stronger than the forces between water molecules. Ionic liquids usually exhibit extremely low vapor pressure.

Ionic liquids exhibit some degree of polarity depending on the composition of the cations and the anions. Ionic liquids have good solubility for a range of polar and non-polar compounds. Many ionic liquids can be used as solvents for Hydride (such as NaH and $CaH_2$), carbides, nitrides, sulfides and various oxide salts, which are extremely difficult to be dissolved in ordinary solvents.

Due to the excellent physical and chemical properties of ionic liquids, they can be used in chemical extraction, organic synthesis reactions, and as chemical catalysts. Ionic liquids are considered as new environmentally friendly solvents.

Recent work has shown that ionic liquids can serve as solvents for biocatalytic reactions. There are many reports on the interaction between ionic liquids and enzymes, for example, the effect of ionic liquids on the activity, stability and selectivity of enzymes. But, there are few studies on the application of ionic liquids in terms of antibody stability. At present, small molecule carbohydrates and surfactants are usually used as protective agents for antibody, but the protective effects are not satisfactory. There is a need for an effective and environmentally friendly antibody protective agent.

BRIEF DESCRIPTION OF THE DRAWINGS

FIG. 1 shows the linear regression between the concentration of aflatoxin and the immunoelectrode impedance in the presence of an antibody protective agent. When the concentration of aflatoxin varies from 0.01 μg/L to 2.0 μg/L, the linear regression equation is Y=1.1649X+0.1141 and the linear coefficient is 0.9982.

FIG. 2 shows the linear regression between the concentration of Staphylococcal enterotoxin b and the immunoelectrode impedance in the presence of an antibody protective agent. When the concentration of Staphylococcal enterotoxin b varies from 0.005 μg/L to 1.0 μg/L, the linear regression equation is Y=1.3055X+0.0809 and the linear coefficient is 0.9989.

FIG. 3 shows the linear regression between the concentration of algae toxin and the immunoelectrode impedance in the presence of an antibody protective agent. When the concentration of algae toxin varies from 0.005 μg/L to 1.0 μg/L, the linear regression equation is Y=0.9964X+0.1063 and the linear coefficient is 0.9985.

FIG. 4 shows the linear regression between the concentration of vomitoxin and the immunoelectrode impedance in the presence of an antibody protective agent. When the concentration of vomitoxin varies from 0.005 μg/L to 1.0 μg/L, the linear regression equation is Y=1.1309X+0.1038, the linear coefficient is 0.9965.

DETAILED DESCRIPTION

The present invention provides an antibody protective agent comprising an ionic liquid, which maintains the stability and activity of antibodies at room temperature.

The antibody protective agent of the invention comprises an ionic liquid, 1-sec-butyl-3-methylimidazolium hexafluorophosphate. In one embodiment of the invention, the concentration of 1-sec-butyl-3-methylimidazolium hexafluorophosphate varies from 0.05% to 5% (v/v).

The antibody protective agent of the invention further comprises bovine serum albumin, thimerosal and phosphate buffered saline (PBS) (pH7.4). In an embodiment of present invention, the concentration of 1-sec-butyl-3-methylimidazolium hexafluorophosphate, bovine serum, and thimerosal varies from 0.05% to 5% (v/v), 0.1 g/L to 3 g/L, and 0.05 g/L to 1 g/L, respectively.

The antibody protective agent of the invention further comprises calcium chloride and trehalose, wherein the concentration of calcium chloride and trehalose varies from 10 mmol/L to 30 mmol/L and 200 mmol/L to 600 mmol/L, respectively.

In a preferred embodiment of the antibody protective agent, the concentration of 1-sec-butyl-3-methylimidazolium hexafluorophosphate, bovine serum albumin, thimerosal, calcium chloride, and trehalose are 0.5% (v/v), 1 g/L, 0.1 g/L, and 20 mmol/L and 500 mmol/L, respectively.

The method of synthesizing 1-sec-butyl-3-methylimidazolium hexafluorophosphate was described in Zhao et al. (Microwave-Assisted Synthesis, Crystal Structure and Thermal Stability of Ionic Liquid 1-sec-butyl-3-methylimidazolium hexafluorophosphate, Chemical Journal of Chinese Universities, 2009, 9:1814-1818). Briefly, equal molar of N-methylimidazole and 1-bromobutane is mixed in a heated flask with an electronic mixer, a thermometer, and high purity nitrogen gas. Continue mixing until the solution changes from transparent to paste-like, and add water to dissolve the reaction product. Discard the upper layer of un-reacted raw material, and transfer the reaction product to a 400 ml beaker. Add 200 ml acetone to the 400 ml beaker and mixed the solution. Add potassium hexafluorophosphate solution in batches while stirring. Continue mixing the solution for three hours, and then remove potassium bromide from the reaction solution by filtration. Acetone is later removed from the filtrate by vacuum distillation. The resulting product is a colorless ionic liquid, 1-sec-butyl-3-methylimidazolium hexafluorophosphate, which can be analyzed and characterized by UV, IR infrared, 1H-NMR analysis techniques and electrospray ionization mass spectrometry.

The invention provides a method of making an immunoelectrode, which enhances the stability of the immunoelectrode.

The method of making an immunoelectrode comprises: a) mixing an antibody with an antibody protective agent at the ratio from 1:1 to 1:3 (v/v) to make a protective antibody mixture; b) coating a bare gold electrode with the protective antibody mixture to make a working electrode for immunological detection.

A method of making a working electrode comprising: a) polishing a gold electrode (the diameter is 2 mm) sequentially in 0.3 and 0.05 μM alumina ($Al_2O_3$) suspension; b) washing the electrode by ultrasound treatment for 5 minutes each in distilled water, ethanol and distilled water; c) air-drying the electrode at room temperature; d) coating the surface of the electrode with carboxylated carbon nanotubes and air-drying the electrode at room temperature; e) adding 10 μl of the above protective antibody mixture to the surface of the electrode and incubating at 37° C. for 1 hour; f) washing the electrode in distilled water and store the electrode at 4° C.

An immunoelectrode coated with an antibody has certain impedance value. Interaction of the antibody and its antigen causes the change of the impedance of the antibody-coated immunoelectrode, which is proportional to the antigen concentration (Ionescu R E, Jaffrezic-Renault N, Bouffier L, et al. Impedimetric immunosensor for the specific label free detection of ciprofloxacin antibiotic. Biosensors and Bioelectronics, 2007, 23: 549-555.). The concentration of the antigen can be determined by measuring the change of the immunoelectrode impedance caused by the interaction between the antigen and its antibody. Impedance can be measured using an impedance spectroscopy, for example, in a CHI 760C electrochemical workstation (CH Instruments Inc., USA).

A method of immunological detection of an antigen comprising: a) immersing an antibody-coated electrode in the antigen solutions with various predetermined concentrations; b) measuring the impedance of the antibody-coated electrode; c) making a linear regression between the antibody-coated electrode impedance and the antigen concentrations to obtain a linear regression equation; d) determining an unknown concentration of the antigen from the linear regression equation by measuring the impedance of the antibody-coated electrode immersed in the unknown antigen solution.

The immunological detection method can be, for example, an enzyme-linked immunosorbent assay (ELISA). ELISA is a biochemical method used to detect the presence of an antibody or an antigen in a sample, which is based on the association of the immobilized antibody or antigen and the enzyme-linked antigen or antibody. An antibody or an antigen immobilized to the surface of immobilization carrier can maintain the immunological binding activity. An antibody or an antigen labeled with an enzyme not only has the immunological binding activity but also the enzymatic activity. The presence of an antibody or an antigen can be detected by measuring the product of the enzymatic reaction when the immobilized antigen or antibody binds to the enzyme-linked antibody or antigen, respectively. The antibody protective agent of present invention can stabilize and maintain the immunological activity of an antibody, thereby enhancing the stability and accuracy of the immunological detection.

The invention uses ionic liquids to develop a new, effective, and environmentally friendly antibody protective agent. The antibody protective agent renders protected antibody to maintain relatively high immunological activity at room temperature. Furthermore, electrodes coated with a mixture of the antibody protective agent and antibodies are installed in immunological detection instruments to significantly enhance the stability and accuracy of the instrument.

EXAMPLES

Example 1

The Determination of Antibody Titer

The activity of an antibody (antibody titer) was determined as described in the following steps.

1) Antigen Coating: dilute antigen 1:4000 in 0.05 M carbonate buffer (pH 9.6). Coat the wells of a flat-bottom 96-well, micro titer plate with 100 μl diluted antigen solution/well. Cover the plate and incubate at 4° C. overnight.

2) Blocking: remove the coating solution, and wash twice the plate for two minutes with 200 μl PBS at room temperature. The washing solution is removed by flicking the plate over a sink. The remaining solution is removed by patting the plate on a paper towel. Block the remaining protein-binding sites in the coated wells by adding 250 μl blocking buffer (3% Bovine Serum Albumin/PBS) per well. Incubate for 2 hours at 37° C.

3) Adding primary antibody: cool down the coated plate to room temperature and wash the plate 3 times with PBS. Add 100 μl/well to different wells with each of the following solutions: antibody dilution solution (0.1% Bovine Serum Albumin/PBS), optimally diluted antibody solution (positive serum), and diluted serum without antibody (negative serum). Incubate for 60 min at 37° C.

4) Adding secondary antibody: wash the plates four times with PBS. Add 100 μl HRP-labeled secondary antibody (diluted by 1:5000) against the primary antibody to each well. Incubate for 30 min at 37° C.

5) Cool down the plate to room temperature. Wash the plate four times with PBS. Dispense 100 μl of the substrate solution (4-methyl-Benzidine solution) per well with a multichannel pipette or a multi-pipette. Incubate at 37° C. for 15 min. Add 50 μl of stop solution (2 M sulfuric acid) per well to stop the reaction.

6) Measuring the antibody titer: read absorbance of each well at the wavelength of 450 nm. When the absorbance is greater than 0.1 and the absorbance of the positive serum is 2.1-fold of that of the negative serum, the corresponding antibody dilution ratio is the antibody titer.

Example 2

An Antibody Protective Agent with 0.5% (v/v) Ionic Liquids

In this example, the concentration of ionic liquids in the antibody protective agent was 0.5% (v/v). Specifically, the antibody protective agent contained 0.5% (v/v) 1-sec-butyl-3-methylimidazolium hexafluorophosphate, 1 g/L bovine serum albumin, 0.1 g/L thimerosal, 20 mmol/L calcium chloride and 500 mmol/L trehalose.

The antibody protective agent was mixed with the antibody serum (algae toxin antibody) at a ratio of 2:1 (v/v) to make a test sample. There was no antibody protective agent in the control sample. The test sample and control sample were left at room temperature for 12 months. The antibody titers of both samples were measured every three months.

Comparison of the antibody titers of the test and the control samples is shown in Table 1. In the first three months, there was no change in antibody activity in the test sample while the antibody activity of the control sample was reduced by 50%. The antibody of the control sample rotted after 6 months, while the antibody of the test sample maintained 94% of the antibody activity after 12 months of storage.

TABLE 1

Comparison of antibody activity with and without the antibody protective agent

| Antibody Storage time | Test sample | Control Sample |
|---|---|---|
| 0 | 64000 | 64000 |
| 3 month | 64000 | 30000 |
| 6 month | 64000 | 0 |
| 9 month | 62000 | 0 |
| 12 month | 60000 | 0 |

Example 3

An Antibody Protective Agent with 0.05% (v/v) Ionic Liquids

In this example, the concentration of ionic liquid in the antibody protective agent was 0.05% (v/v). Specifically, the antibody protective agent contained 0.05% (v/v) 1-sec-butyl-3-methylimidazolium hexafluorophosphate, 1 g/L bovine serum albumin, 0.1 g/L thimerosal, 20 mmol/L calcium chloride and 500 mmol/L trehalose.

The antibody protective agent was mixed with the antibody serum (algae toxin antibody) at a ratio of 2:1 (v/v) to make a test sample. There was no antibody protective agent in the control sample. The test sample and control sample were left at room temperature for 12 months. The antibody titers of both samples were measured every three months.

As shown in table 2, there was no reduction of antibody activity in the test sample after 3 month of storage. The antibody in the test sample retained 87.5% and 78.1% of its antibody activity after 9 months and 12 months of storage, respectively.

TABLE 2

Comparison of antibody activity with and without the antibody protective agent

| Antibody Storage time | Test sample | Control Sample |
|---|---|---|
| 0 | 64000 | 64000 |
| 3 month | 64000 | 30000 |
| 6 month | 60000 | 0 |
| 9 month | 56000 | 0 |
| 12 month | 50000 | 0 |

Example 4

An Antibody Protective Agent with 5% (v/v) Ionic Liquids

In this example, the concentration of ionic liquid in the antibody protective agent was 5% (v/v). Specifically, the antibody protective agent contained 5% (v/v) 1-sec-butyl-3-methylimidazolium hexafluorophosphate, 1 g/L bovine serum albumin, 0.1 g/L thimerosal, 20 mmol/L calcium chloride and 500 mmol/L trehalose.

The antibody protective agent was mixed with the antibody serum (algae toxin antibody) at a ratio of 2:1 (v/v) to make a test sample. There was no antibody protective agent in the control sample. The test sample and control sample were left at room temperature for 12 months. The antibody titers of both samples were measured every three months.

As shown in table 3, the antibody in the test sample retained 87.5%, 75% and 62.5% of its antibody activity after 3 months, 9 months and 12 months of storage, respectively.

TABLE 3

Comparison of antibody activity with and without the antibody protective agent

| Antibody Storage time | Test sample | Control Sample |
|---|---|---|
| 0 | 64000 | 64000 |
| 3 month | 56000 | 30000 |
| 6 month | 50000 | 0 |
| 9 month | 48000 | 0 |
| 12 month | 40000 | 0 |

Example 5

Algae Toxin Antibody and the Antibody Protective Agent Mixed at a Ratio of 1:1 (v/v)

The antibody protective agent contained 0.5% (v/v) 1-sec-butyl-3-methylimidazolium hexafluorophosphate, 1 g/L bovine serum albumin, 0.1 g/L thimerosal, 20 mmol/L calcium chloride and 500 mmol/L trehalose.

Algae toxin antibody was mixed with the antibody protective agent at a ratio of 1:1 (v/v) to make a protective antibody mixture. An electrode was coated with the protective antibody mixture as described in the specification above. The immunoelectrode was stored at room temperature for 12 months. The impedance value of the immunoelectrode was measured every three months.

As shown in table 4, the impedance value of the immunoelectrode was decrease by 50% after 12 months.

TABLE 4

| Impedance value of the immunoelectrode coated by algae toxin antibody mixed with the antibody protective agent at a ratio of 1:1 (v/v) | |
|---|---|
| storage time | immunoelectrode impedance value/kΩ |
| 0 | 1.6 |
| 3 month | 1.2 |
| 6 month | 1.1 |
| 9 month | 0.9 |
| 12 month | 0.8 |

Example 6

Algae Toxin Antibody and the Antibody Protective Agent Mixed at a 1:2 Ratio (v/v)

The antibody protective agent contained 0.5% (v/v). 1-sec-butyl-3-methylimidazolium hexafluorophosphate, 1 g/L bovine serum albumin, 0.1 g/L thimerosal, 20 mmol/L calcium chloride and 500 mmol/L trehalose Algae toxin antibody was mixed with the antibody protective agent at a ratio of 1:2 (antibody:protective agent) to make a protective antibody mixture. An electrode was coated with the protective antibody mixture as described in the specification above. The immunoelectrode was stored at room temperature for 12 months. The impedance value of the immunoelectrode was measured every three month.

As shown in table 5, the impedance value of the immunoelectrode was decrease by 17% after 12 months.

TABLE 5

Impedance value of the immunoelectrode coated by algae toxin antibody mixed with the antibody protective agent at a 1:2 ratio

| storage time | immunoelectrode impedance value/kΩ |
| --- | --- |
| 0 | 1.6 |
| 3 month | 1.48 |
| 6 month | 1.4 |
| 9 month | 1.36 |
| 12 month | 1.34 |

Example 7

Algae Toxin Antibody and the Antibody Protective Agent Mixed at a 1:3 Ratio (v/v)

The antibody protective agent contained 0.5% 1-sec-butyl-3-methylimidazolium hexafluorophosphate, 1 g/L bovine serum albumin, 0.1 g/L thimerosal, 20 mmol/L calcium chloride and 500 mmol/L trehalose.

Algae toxin antibody was mixed with the antibody protective agent at a ratio of 1:3 (antibody:protective agent) to make a protective antibody mixture. An electrode was coated with the protective antibody mixture as described in the specification above. The immunoelectrode was stored at room temperature for 12 months. The impedance value of the immunoelectrode was measured every three month.

As shown in table 6, the impedance value of the immunoelectrode was decrease by 56% after 12 months

TABLE 6

Impedance value of the immunoelectrode coated by algae toxin antibody mixed with the antibody protective agent at a 1:3 ratio

| storage time | immunoelectrode impedance value/kΩ |
| --- | --- |
| 0 | 1.6 |
| 3 month | 1.3 |
| 6 month | 1.1 |
| 9 month | 0.9 |
| 12 month | 0.7 |

Example 8

Preparation of Immunological Detection Devices

A method of preparing a working electrode comprises the following steps:
A, Polish the gold electrode (the diameter is 2 mm) by 0.3 and 0.05 μM alumina suspension solution;
B, Sonicate the electrode for 5 minutes sequentially in purified water, ethanol and purified water; Air-dry the electrode at room temperature.
C, Add the carboxylated carbon nanotube onto the surface of electrode, and air-dry the electrode at room temperature;
D, Add 10 μl the antibody mixture to the surface of electrode;
E, Incubate the electrode at 37° C. for 1 hour;
F, Wash the electrode in purified water and store at 4° C.

The impedance of the immunoelectrode is measured by the electrochemical workstation CHI760C (CH Instruments Inc., USA). The immunological detection uses a three-electrode system, which comprises of an immunoelectrode as a working electrode, a saturated calomel as a reference electrode, and a platinum wire as a counter electrode. The immunoelectrode coated with antibody has certain impedance value, which changes due to antibody-antigen interaction. Within certain concentration range of the antigen, the change of the immunoelectrode impedance value is proportional to the antigen concentration. The concentration of an unknown antigen concentration can be determined by measuring the change of the immunoelectrode impedance.

Example 9

Application of the Antibody Protective Agent in the Immunological Detection of Aflatoxin The protective agent contained 0.5% (v/v) 1-sec-butyl-3-methylimidazolium hexafluorophosphate, 1 g/L bovine serum albumin, 0.1 g/L thimerosal, 20 mmol/L calcium chloride and 500 mmol/L trehalose.

Aflatoxin antibody was mixed with the antibody protective agent at a ratio of 2:1, and the electrode was coated with the protective antibody mixture. An immunoelectrode was prepared as described in Example 8.

Determine a linear regression equation which reflects the relationship between the concentration of aflatoxin and the immunoelectrode impedance value. As shown in FIG. 1, when the concentration of aflatoxin varies from 0.01 μg/L to 2.0 μg/L, the concentration of aflatoxin is linearly related to the immunoelectrode impedance, with the linear regression equation as $Y=1.1649X+0.1141$ (Y: immunoelectrode impedance; X: concentration of afltexin). The coefficient of the linear regression is 0.9982.

Example 10

Application of the Antibody Protective Agent in the Immunological Detection of Staphylococcal Enterotoxin b The antibody protective agent contained 0.5% 1-sec-butyl-3-methylimidazolium hexafluorophosphate, 1 g/L bovine serum albumin, 0.1 g/L thimerosal, 20 mmol/L calcium chloride and 500 mmol/L trehalose.

Staphylococcal enterotoxin b antibody was mixed with the antibody protective agent at a ratio of 2:1, and the electrode was coated with the protective antibody mixture. An immunoelectrode was prepared as described in Example 8.

Figure 2:
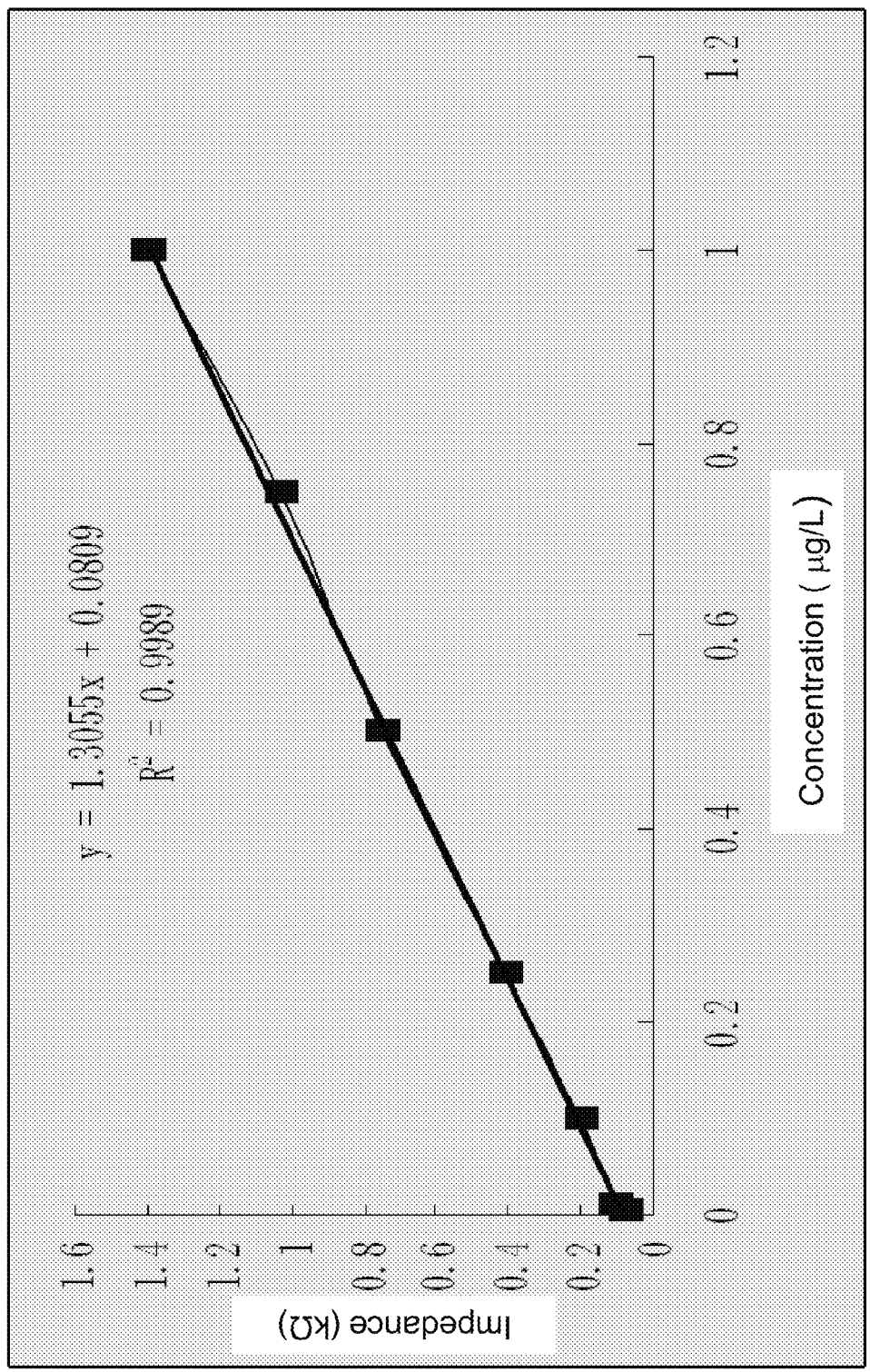

Determine a linear regression equation which reflects the relationship between the concentration of staphylococcal enterotoxin b and the immunoelectrode impedance value. As shown in FIG. 2, when the concentration of staphylococcal enterotoxin b varies from 0.005 μg/L to 1.0 μg/L, the concentration of staphylococcal enterotoxin b is linearly related to the immunoelectrode impedance, with a linear regression equation as $Y=1.3055X+0.0809$ (Y: immunoelectrode impedance; X: concentration of staphylococcal enterotoxin b). The coefficient of the linear regression is 0.9989.

Example 11

Application of the Antibody Protective Agent in the Immunological Detection of Algae Toxin The protective agents contained 0.5% (v/v) 1-sec-butyl-3-methylimidazolium hexafluorophosphate, 1 g/L bovine serum albumin, 0.1 g/L thimerosal, 20 mmol/L calcium chloride and 500 mmol/L trehalose.

Algae toxin antibody was mixed with the antibody protective agent at a ratio of 2:1, and the electrode was coated with the protective antibody mixture. An immunoelectrode was prepared as described in Example 8.

Figure 3:
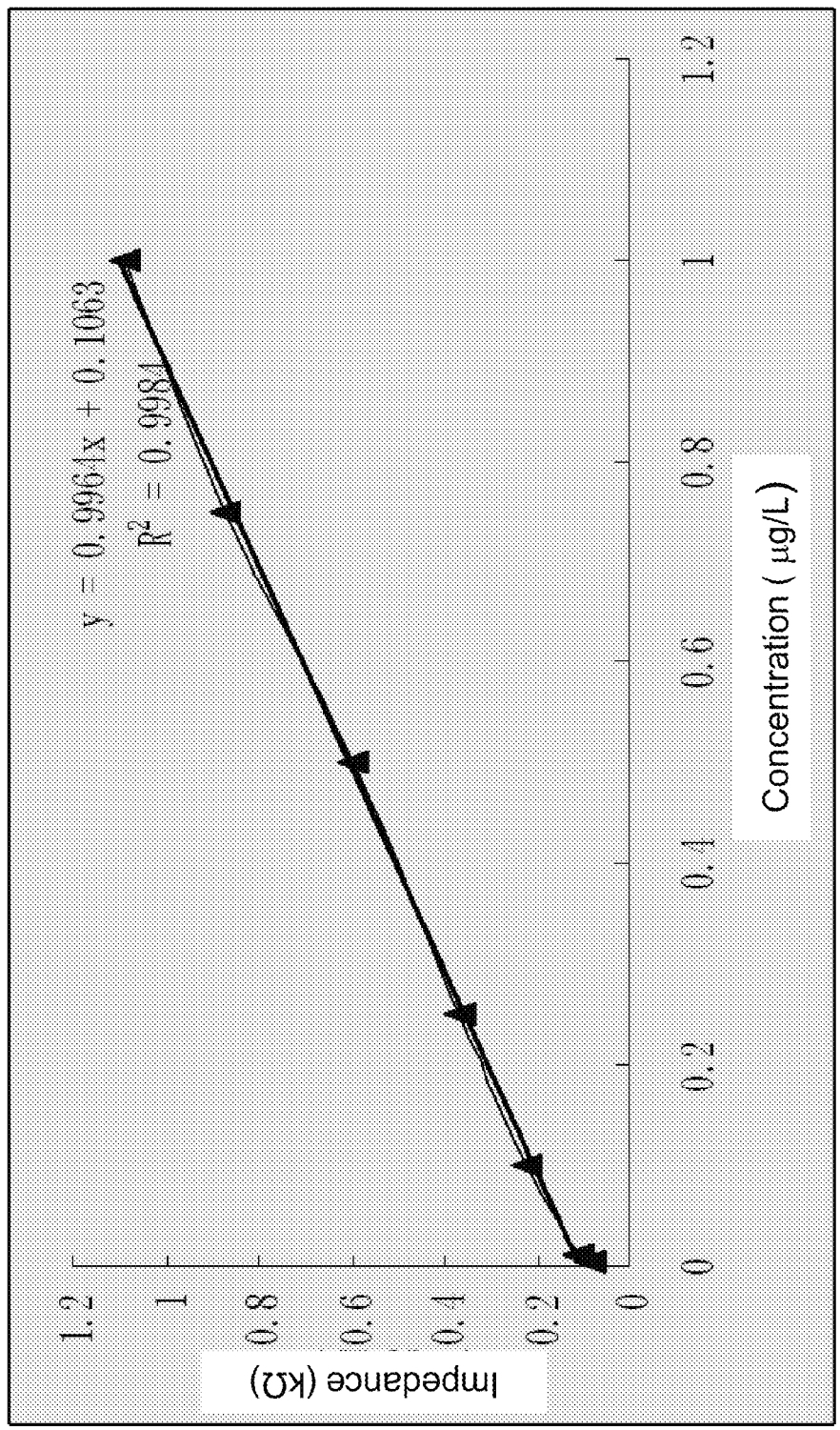

Determine a linear regression equation which reflects the relationship between the concentration of algae toxin and the immunoelectrode impedance value. As shown in FIG. 3, when the concentration of algae toxin varies from 0.005 μg/L to 1.0 μg/L, the concentration of algae toxin is linearly related to the immunoelectrode impedance, with a linear regression equation as Y=0.9964X+0.1063 (Y: immunoelectrode impedance; X: concentration of algae toxin). The coefficient of the linear regression is 0.9985.

Example 12

Application of the Antibody Protective Agent in the Immunological Detection of Vomitoxin The antibody protective agent contained 0.5% (v/v) 1-sec-butyl-3-methylimidazolium hexafluorophosphate, 1 g/L bovine serum albumin, 0.1 g/L thimerosal, 20 mmol/L calcium chloride and 500 mmol/L trehalose.

Vomitoxin antibody was mixed with the antibody protective agent at a ratio of 2:1, and the electrode was coated with the protective antibody mixture. An immunoelectrode was prepared as described in Example 8.

Figure 4:
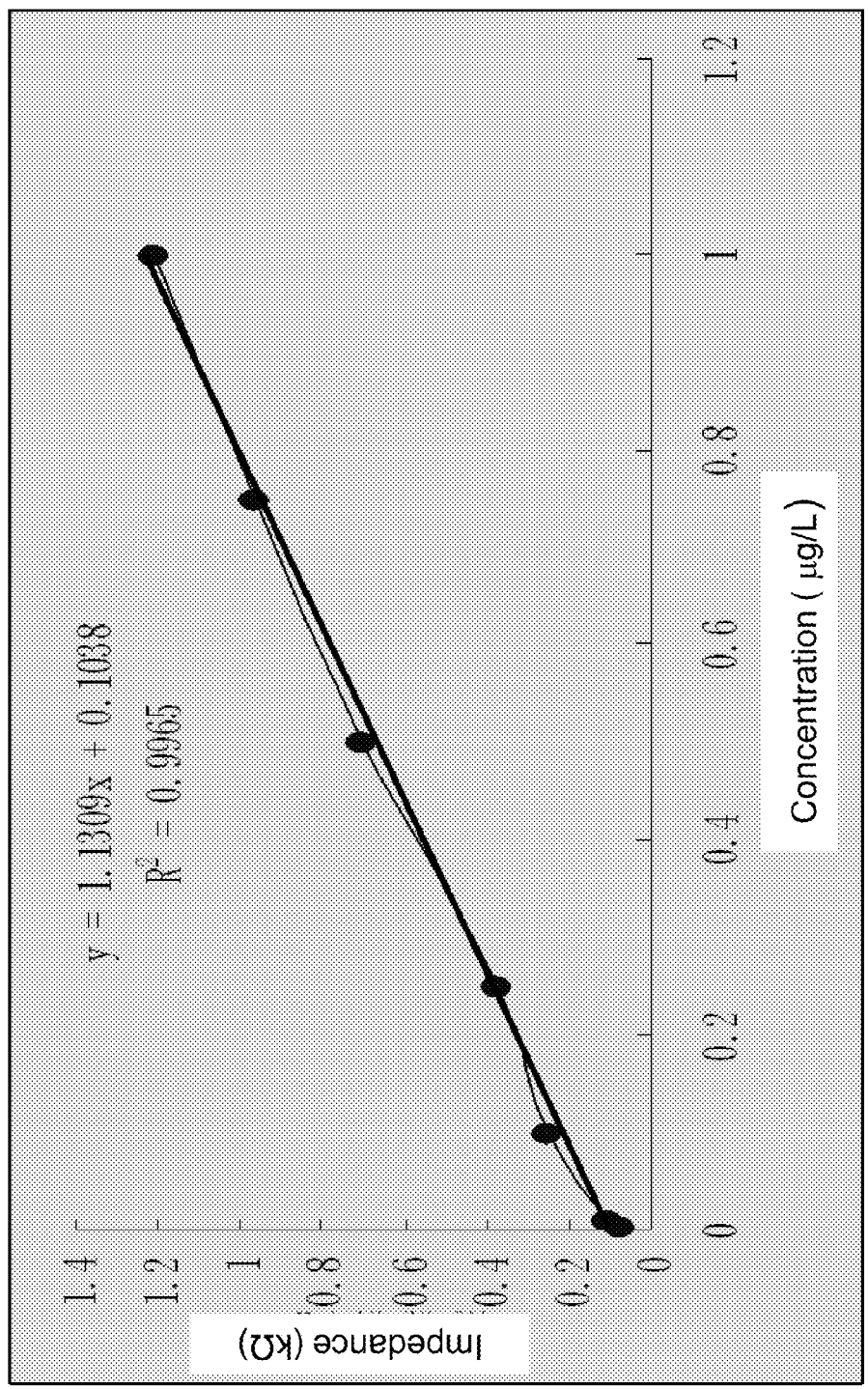

Determine a linear regression equation which reflects the relationship between the concentration of vomitoxin and the immunoelectrode impedance value. As shown in FIG. 4, when the concentration of vomitoxin varies from 0.005 μg/L to 1.0 μg/L, the concentration of vomitoxin is linearly related to the immunoelectrode impedance, with a linear regression equation as Y=1.1309X+0.1038 (Y: immunoelectrode impedance; X: concentration of vomitoxin). The coefficient of the linear regression is 0.9965.

While the present invention has been described in some details for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. An antibody protective agent, comprising: 1-sec-butyl-3-methylimidazolium hexafluorophosphate, bovine serum albumin, thimerosal and phosphate buffered saline (pH7.4).

2. The antibody protective agent of claim 1, wherein the concentration of 1-sec-butyl-3-methylimidazolium hexafluorophosphate, bovine serum albumin, and thimerosal varies from 0.05% (v/v) to 5% (v/v), 0.1 g/L to 3 g/L, and 0.05 g/L to 1 g/L, respectively.

3. The antibody protective agent of claim 1, further comprising calcium chloride and trehalose.

4. The antibody protective agent of claim 3, wherein the concentration of calcium chloride and trehalose varies from 10 to 30 mmol/L and 200 to 600 mmol/L, respectively.

5. The antibody protective agent of claim 4, wherein the concentration of 1-sec-butyl-3-methylimidazolium hexafluorophosphate, bovine serum albumin, thimerosal, Calcium chloride, and trehalose is 0.5% (v/v), 1 g/L, 0.1 g/L, 20 mmol/L, and 500 mmol/L respectively.

6. The antibody protective agent of claim 1, wherein the phosphate buffered saline is comprised of disodium phosphate, sodium dihydrogen phosphate and sodium chloride, and adjusted to pH 7.4.

* * * * *